United States Patent
Yazaki et al.

(10) Patent No.: US 6,498,139 B1
(45) Date of Patent: Dec. 24, 2002

(54) REMEDIES FOR DISEASES CAUSED BY INSULIN RESISTANCE

(75) Inventors: Yoshio Yazaki, Tokyo (JP); Tomoichiro Asano, Tokyo (JP); Hideo Kubo, Tokyo (JP); Akira Kanda, Tokyo (JP)

(73) Assignee: Daiichi Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/508,691

(22) PCT Filed: Sep. 25, 1998

(86) PCT No.: PCT/JP98/04293

§ 371 (c)(1),
(2), (4) Date: Mar. 29, 2000

(87) PCT Pub. No.: WO99/16462

PCT Pub. Date: Apr. 8, 1999

(30) Foreign Application Priority Data

Sep. 29, 1997 (JP) ............................................. 9-263719

(51) Int. Cl.[7] ............................................... A01N 37/18

(52) U.S. Cl. ............................. 514/2; 514/14; 530/300; 530/350; 530/326; 435/7.1; 435/7.8

(58) Field of Search ....................... 514/2, 14; 530/300, 530/350, 326; 435/7.1, 7.8

(56) References Cited

PUBLICATIONS

Wells, JA Additivity of Mutational Effects in Proteins. Biochemistry 29:8509–8517 (1990).*
Araki, et al. Human Skeletal Muscle Insulin Receptor Substrate–1. Characterization of the cDNA, Gene, and Chromosomal Localization. Diabetes vol. 1041–154 (1993).*

* cited by examiner

*Primary Examiner*—Elizabeth Kemmerer
*Assistant Examiner*—Regina M. DeBerry
(74) *Attorney, Agent, or Firm*—Oblon, Spivak, McClelland, Maier & Neustadt, P.C.

(57) ABSTRACT

The present invention provides methods of inhibiting or sequestering 14-3-3 protein from binding to the insulin receptor substrate –1 or –2 by administering a substance which inhibits the interaction of these two proteins.

18 Claims, No Drawings

REMEDIES FOR DISEASES CAUSED BY INSULIN RESISTANCE

The present application is a 371 of PCT/JP98/04293 filed Sep. 25, 1998.

TECHNICAL FIELD

The present invention relates to a drug, particularly a remedy for diseases caused by insulin resistance, such as diabetes, as well as to a screening method for the remedy.

BACKGROUND ART

Insulin is a hormone which regulates the concentration of blood sugar and blood lipid through the promotion of glucose and lipid intake into cells and utilization and storage of them. Insulin resistance indicates the condition in which insulin does not act normally on cells, and this condition causes elevation of the concentration of blood sugar or blood lipid. Examples of diseases caused by insulin resistance include diabetes, diabetic microangiopathies (diabetic nephropathy, diabetic neuropathy, and diabetic retinopathy), impaired glucose tolerance, hyperinsulinemia, hyperlipemia, arteriosclerosis, hypertension, obesity, ischemic heart diseases, ischemic brain disorders, and peripheral arterial embolism (Tamio Teramoto, et al., (1995) Biomedicine & Therapeutics 29, 8–96). The cause of insulin resistance has not yet been fully elucidated, and causal therapy thereof has not been developed.

Recently, abnormality of intracellular signal transduction induced by insulin has become of interest as a cause of insulin resistance. In signal transduction of insulin, the first response induced by insulin is activation of insulin receptor tyrosine kinase. Subsequently, several intracellular substrates including insulin receptor substrate-1 (IRS-1) (Sun, X. et al., (1991) Nature 352, 73–77) and insulin receptor substrate-2 (IRS-2) (Sun, X. et al., (1995) Nature 377, 173–177) are phosphorylated. IRS-1 and IRS-2 have potential tyrosine-phosphorylated sites in amounts of 21 and 23, respectively, and they function as "docking protein" which transmits insulin signals to several proteins having Src-homology 2 domains (SH2-protein) (Sun, X. et al., (1993) Mol. Cell. Biol. 13, 7418–7428).

However, the function of IRS-1 and IRS-2 relating to insulin signal transduction in the aforementioned action is not necessarily fully elucidated, and elucidation of novel function thereof and development of drugs on the basis of the function are demanded.

An object of the present invention is to elucidate novel function of IRS-1 and IRS-2, and to provide a drug based on the function.

DISCLOSURE OF THE INVENTION

In view of the foregoing, the present inventors have focused on the relation between IRS-1 or IRS-2 and 14-3-3 protein.

14-3-3 Protein is widely distributed in eucaryotes such as animals, plants, ahd yeast, and is a protein family which is supposed to act as a regulatory factor by binding to a particular target protein in a variety of signal transductions depending on phosphorylation and dephosphorylation of proteins (Fumiko Shinkai, et al., (1996) Protein Nucleic Acid Enzyme 41, 313–326). Recently, it has been reported that 14-3-3 protein binds to phosphatidylinositol 3-kinase (PI3K) and inhibits its activity in T lymphocytes (Bonnefoy-Berard, N. et al., (1995) Proc. Natl. Acad. Sci. 92, 10142–10146). PI3K plays an important role in signal transduction of insulin (Masato Kasuga, (1996) Saishin-Igaku 51, 1564–1572), and thus 14-3-3 protein has been supposed to effect some type of regulation against signal transduction of insulin (Humiko Shinkai, et al., (1996) Protein Nucleic Acid Enzyme 41, 313–326). In addition, very recently, it has been reported that the $\epsilon$ isoform of 14-3-3 protein binds to IRS-1, but the physiological significance has not been elucidated (Craparo, A. (1997) J. Biol. Chem. 272. 11663–11669).

The present inventors have performed extensive studies on the relation between 14-3-3 protein and IRS-1 or IRS-2; have elucidated that IRS-1 or IRS-2 binds to 14-3-3 protein at a particular site and that the binding effects negative regulation against insulin signal transduction; and have found that a substance inhibiting the binding is useful for a remedy for diseases caused by insulin resistance. The present invention has been accomplished on the basis of these findings.

Accordingly, the present invention provides a remedy for diseases caused by insulin resistance, which comprises, as an active ingredient, a substance exhibiting activity for inhibiting the binding of the full-length IRS-1 or IRS-2 or a portion of the same to the full-length 14-3-3 protein or a portion of the same.

The present invention also provides a screening method for a remedy for diseases caused by insulin resistance, which comprises assaying activity for inhibiting the binding of the full-length IRS-1 or IRS-2 or a portion of the same to the full-length 14-3-3 protein or a portion of the same.

The present invention also provides a pharmaceutical composition for diseases caused by insulin resistance, which comprises a substance exhibiting activity for inhibiting the binding of the full-length IRS-1 or IRS-2 or a portion of the same to the full-length 14-3-3 protein or a portion of the same, and a pharmaceutically acceptable carrier.

The present invention also provides use of a substance exhibiting activity for inhibiting the binding of the full-length IRS-1 or IRS-2 or a portion of the same to the full-length 14-3-3 protein or a portion of the same for producing a remedy for diseases caused by insulin resistance.

The present invention also provides a method for treating diseases caused by insulin resistance, which comprises administering to a patient in need thereof an effective dose of a substance exhibiting activity for, inhibiting the binding of the full-length IRS-1 or IRS-2 or a portion of the same to the full-length 14-3-3 protein or a portion of the same.

BEST MODE FOR CARRYING OUT THE INVENTION

Active ingredients of the remedy of the present invention include a substance exhibiting activity for inhibiting the binding of the full-length IRS-1 or IRS-2 or a portion of the same to the full-length 14-3-3 protein or a portion of the same in screening for assaying the inhibiting activity.

As described below, the present inventors were the first to elucidate that the binding of 14-3-3 protein to IRS-1 or IRS-2 effects negative regulation against insulin signal transduction.

Firstly, in order to identify a unique protein that binds to IRS-1, the present inventors used $^{32}$P-labeled recombinant IRS-1 as a probe in order to screen a cDNA library derived from human heart, to thereby obtain two isoforms ($\epsilon$ and $\zeta$) which belong to a 14-3-3 protein family. In addition, they found that 14-3-3 protein associates with IRS-1 in L6 muscular cells, HepG2 hepatoma cells, and Chinese hamster ovary cells, in which IRS-1 is overexpressed by means of an adenovirus expression system, as well as in the brain tissue of cow in a natural state.

The present inventors also elucidated that 14-3-3 protein associates with IRS-1 or IRS-2 in SF9 cells in which 14-3-3 protein and IRS-1 or IRS-2 are overexpressed by means of a baculovirus expression system.

The present inventors also elucidated, by use of HepG2 hepatoma cells in which IRS-1 is overexpressed in the same manner as described above, that the amount of 14-3-3 protein binding to IRS-1 is not changed by insulin stimulation, and that the amount is significantly increased by okadaic acid, which is an inhibitor of serine/threonine phosphatase.

The present inventors also elucidated that IRS-1 has three putative binding sites (Ser-270, Ser-374, and Ser-641) for 14-3-3 protein, on the basis of the finding that, in a cell lysate of L6 muscular cells, the binding of IRS-1 to 14-3-3 protein fused with glutathione S-transferase (GST) is inhibited by three types of 15-residue oligopeptide shown in sequence Nos. 2–4 which contains a serine residue and several amino acid residues in the vicinity of it corresponding to the amino acid sequence of IRS-1, and the serine residue is phosphorylated. Of the above three binding sites, the motif around of Ser-270 are located in the phosphotyrosine binding domain (PTB domain) of IRS-1, and the domain is known to play an important role in interaction with insulin receptors (Wolf, G. (1995) J. Biol. Chem. 270, 27407–27410). The present inventors elucidated that, in practice, truncated IRS-1 containing the PTB domain and 205 amino acids adjacent to its C-terminal side associates with GST-fused 14-3-3 protein, by overexpressing the IRS-1 in HepG2 hepatoma cells by means of an adenovirus expression system.

In addition, the present inventors found that IRS-1 that has been coprecipitated with an antibody against 14-3-3 protein is insusceptible to phosphorylation of serine and tyrosine residues by insulin stimulation as compared with IRS-1 that has been coprecipitated with an antibody against IRS-1, by analyzing the effect of the binding of 14-3-3 protein to IRS-1 on phosphorylation of IRS-1 induced by insulin, and analyzing phosphorylated amino acids in a HepG2 hepatoma cell in which IRS-1 is overexpressed by means of an adenovirus expression system. As described above, it was elucidated that 14-3-3 protein effects negative regulation against insulin signal transduction by inhibiting the association of insulin receptors with IRS-1.

Therefore, abnormal promotion of the binding of 14-3-3 protein to IRS-1 or IRS-2 is a primary cause for insulin resistance, and thus insulin resistance may be suppressed and diseases caused by insulin resistance may be treated by inhibiting, suppressing, and dissociating the binding. In order to inhibit the binding, direct inhibition may be effected against the binding of 14-3-3 protein to IRS-1 or IRS-2. Alternatively, indirect inhibition may be effected; for example, phosphorylation of a particular serine residue in the amino acid sequence of IRS-1 or IRS-2, which phosphorylation is considered to play an important role in the binding of 14-3-3 protein to IRS-1 or IRS-2, may be inhibited, or dephosphorylation may be promoted.

The full-length IRS-1 or IRS-2 or a portion of the same used in the present invention may be obtained, for example, by means of the following procedure: cDNA coding for the full-length IRS-1 or IRS-2 or a portion of the same is introduced into baculovirus by means of known methods, and the full-length IRS-1 or IRS-2 or a portion of the same is isolated from the insect cells infected with the virus and purified by means of known methods. The amino acid sequence of IRS-1 is shown in sequence No. 1. When a portion of IRS-1 or IRS-2 is oligopeptide, the portion may be synthesized by means of known peptide synthesis methods. A portion of IRS-1 or IRS-2 may be peptides containing a serine residue in the amino acid sequence of IRS-1 or IRS-2, or phosphorylated products of the peptides. Preferably, a portion of IRS-1 or IRS-2 may be peptide containing the PTB domain (amino acid 161-517 in sequence No. 1 in the case of IRS-1, the amino acid sequence in sequence No. 5 in the case of IRS-2 (corresponding to amino acid 196-354 of IRS-2)), more preferably oligopeptides containing Ser-270, Ser-374, or Ser-641 of IRS-1, or phosphorylated products of the peptides. The length of the portion is not limited so long as activity for inhibiting the binding can be assayed with high sensitivity, and the portion may be 5–50 amino acids, preferably 10–30 amino acids, more preferably 15 amino acids containing serine which is phosphorylated.

The full-length 14-3-3 protein or a portion of the same used in the present invention may be obtained, for example, by means of the following procedure: cDNA coding for the full-length 14-3-3 protein or a portion of the same is introduced into baculovirus by means of known methods, and the full-length 14-3-3 protein or a portion of the same is isolated from the insect cell infected with the virus and purified by means of known methods. A portion of 14-3-3 protein may be the box-1 region which is the binding site to tryptophan hydroxylase (Ichimura, T. et al., (1997) FEBS Lett. 413, 273–276), or a peptide containing the region.

In order to obtain the full-length IRS-1 or IRS-2 or a portion of the same, and the full-length 14-3-3 protein or a portion of the same, they may be advantageously expressed as a fusion protein in a variety of gene expression systems. Fusion protein expression systems such as those including lactose and glutathione S-transferase may also be used.

In order to prepare the aforementioned screening system, the full-length labeled IRS-1 or labeled IRS-2 or a portion of the same, or the full-length labeled 14-3-3 protein or a portion of the same is preferably used. $^{125}$I or an enzyme which is often used in enzyme immunoassay, such as alkaline phosphatase, is appropriately used for labeling. Such a substance for labeling is bonded to the protein by means of known methods. When the labeled protein is not used, a primary antibody specific to the unlabeled protein and a secondary antibody which is labeled and recognizes the primary antibody are necessary. The primary and secondary antibodies may be commercially available ones.

Next will be described a preferred embodiment for effecting screening for a substance exhibiting activity for inhibiting the binding of 14-3-3 protein to IRS-1 or IRS-2 by means of the above-described system. Firstly, IRS-1 or IRS-2 (the full length or a portion thereof), or 14-3-3 protein (the full length or a portion thereof) is prepared by immobilization thereof onto a plastic material (a microplate or beads) by means of a known method. Subsequently, the other protein to be bonded which is labeled is dissolved in an appropriate buffer, and the resultant solution is added to each well of a microplate (when a microplate is used) or to test tubes containing the beads (when beads are used). A test compound is also added thereto. Independently, a solution containing a very large amount of unlabeled protein is prepared in order to determine the amount of non-specific binding (NSB). The solution containing the labeled protein is incubated under appropriate conditions, and the material (each well of the microplate, or the beads) is washed with the buffer. The amount of the labels attached to the protein binding to the well or beads is measured by means of known methods. When the labeled protein is not used, the solution containing the unlabeled protein is incubated in the same manner, an antibody specific to the unlabeled protein (the primary antibody) is added, and the solution is incubated under appropriate conditions. Furthermore, the secondary antibody which is labeled and recognizes the primary antibody is added, and the solution is incubated under appropriate conditions. Thereafter, the substrate is washed with the buffer, and the amount of labels attached to the protein binding to the substrate is measured in the same manner. When the value of "Bo—NSB" —which is obtained by subtracting NSB from the amount of labels attached to the protein to be bonded in the absence of a binding-inhibitory substance (Bo)—is regarded as 100%, a test compound providing the value (amount of specific binding) of 10% or less may be chosen as a substance exhibiting activity for inhibiting the binding.

A substance source which is considered to exhibit the binding inhibitory activity may be tested by means of the above-described screening system. Examples of such a substance source include synthetic peptides, low-molecular organic compounds, and natural products, preferably substances having applicability as drugs. Specific examples include combinatorial libraries of different chemical substances and synthetic peptide libraries.

A substance exhibiting the binding inhibitory activity which is obtained by means of the above-described screening suppresses negative regulation against insulin signal transduction in cells. Therefore, the substance is useful for producing a remedy for diseases caused by insulin resistance. Examples of such diseases include diabetes, diabetic microangiopathies (diabetic nephropathy, diabetic neuropathy, and diabetic retinopathy), impaired glucose tolerance, hyperinsulinemia, hyperlipemia, arteriosclerosis, hypertension, obesity, ischemic heart diseases, ischemic brain disorders, and peripheral arterial embolism.

A dosage of the remedy of the present invention depends on the age, sex, and pathological condition of a patient, and is 5 mg-2 g per adult per day, preferably 50–100 mg as reduced to an active ingredient. The aforementioned dosage per day may be administered in a single portion once a day, or in divided portions 2–3 times a day. If necessary, a dosage per day may exceed the aforementioned dosage.

No particular limitation is imposed on the administration method and the dosage form of the remedy of the present invention, and any dosage form suitable for an administration method may be obtained by means of a conventionally used technique for preparing products.

Examples of products for oral administration include tablets, powders, granules, capsules, solutions, syrups, elixirs, and oily or aqueous suspensions.

For preparation of injections, a solution may be stored in a container and freeze-dried, to thereby provide a solid product, and the solid product may be prepared into an injection just before use. If necessary, the product may contain a stabilizer, a preservative, and a solubilizer. A single dosage of the injection product may be stored in a container, or a plurality of dosages may be stored in the same container.

Examples of external-use products include solutions, suspensions, emulsions, ointments, gels, creams, lotions, and sprays.

Solid products may contain pharmaceutically acceptable additives together with an active ingredient. If necessary, the remedy may optionally contain fillers, expanders, binders, disintegrants, dissolution-promoting agents, humectants, and lubricants, to thereby prepare products.

Examples of liquid products include solutions, suspensions, and emulsions, and the products may contain additives such as suspending agents and emulsifying agents.

EXAMPLES

The present invention will next be described in more detail by way of examples, which should not be construed as limiting the invention thereto.

Example 1

(Method for screening inhibitors for the binding of 14-3-3 protein to IRS-1 or IRS-2 characterized by employing the full-length IRS-1 or IRS-2 or a portion of the same and the full-length 14-3-3 protein or a portion of the same)

A solution containing a portion of human IRS-1, i.e., a portion including the PTB domain (amino acids 161-517) (1 µg/ml, pH 8.0, 50 mM $K_2PO_4$) (100 µl) is added to each well of a 96-well microplate, and the plate is allowed to stand at room temperature for one hour, to thereby cause the human IRS-1 to be fixed onto the walls of the wells. The solution in each well is removed and the well is washed three times with a buffer (50 mM HEPES, 150 mM NaCl, 0.1% Triton X-100) (300 µl). Subsequently, a buffer solution containing 0.5% bovine serum albumin (BSA) (300 µl) is added to each well and the plate is allowed to stand at room temperature for one hour, to thereby effect blocking. The solution is removed, and each well is washed three times with a buffer (300 µl). Next, a buffer solution containing full-length human 14-3-3 protein (1 µg/ml) (50 µl) and a buffer containing a target sample for screening (50 µl) are simultaneously added to the well and allowed to stand at room temperature for two hours. Independently, a buffer (50 µl) not containing the sample is added to another well which has been treated in the same manner as described above, and allowed to stand, in order to measure the amount of maximum binding (Bo). In order to measure the amount of non-specific binding (NSB), a well to which a portion including the PTB region has not been fixed is subjected to the above-described treatment after blocking, and a buffer solution containing human 14-3-3 protein (50 µl) and a buffer (50 µl) are added to the well, and allowed to stand. Solutions in the above wells are removed, and the wells are washed three times with a buffer (300 µl). A buffer solution containing an anti-human 14-3-3 rabbit polyclonal antibody (Santa Cruz Biotechnology) (0.2 µg/ml) (100 µl) is added to each of the above wells, and the plate is allowed to stand at room temperature for one hour. The solution is removed and the well is washed three times with a buffer (300 µl). Subsequently, a buffer solution containing an alkaline-phosphatase-labeled anti-rabbit IgG goat polyclonal antibody (Linco) (1 µg/ml) (100 µl) is added to each of the wells, and allowed to stand at room temperature for one hour. The solution is removed and the well is washed three times with a buffer (300 µl). After a p-nitrophenyl phosphate solution (1 mg/ml, 1M diethanolamine) (100 µl) is added to each of the wells, the well is allowed to stand at 37° C. for 30 minutes, and a 5% EDTA aqueous solution (100 µl) is added, to thereby terminate the reaction. The absorbance of the resultant product in each well is measured at a wavelength of 405 nm, and the absorbance is regarded as the amount of binding. The binding amount when a sample is added is represented by B. A percentage of binding inhibition by the sample is obtained by the following formula. When the percentage is 10% or less, the sample is selected as a candidate for a substance used in the present invention.

Binding inhibitory percentage (%)=(1-(B-NSB)/(Bo-NSB))×100

Example 2

Three types of synthetic peptide shown in sequence Nos. 2–4 were obtained by use of reagents for peptide synthesis (for example, a peptide block, peptides and amino acids with protective groups, and phosphorylated serine; products of PerkinElmer) by means of a peptide synthesizer (Model: PerkinElmer 433A, product of PerkinElmer). Activity of these peptides ware assayed by means of the binding inhibition screening system described in Example 1. These synthetic peptides exhibit the binding inhibitory activity.

Industrial Applicability

By means of the screening method of the present invention, there can be obtained a remedy for diseases caused by insulin resistance, such as diabetes, diabetic microangiopathies (diabetic nephropathy, diabetic neuropathy, and diabetic retinopathy), impaired glucose tolerance, hyperinsulinemia, hyperlipemia, arteriosclerosis, hypertension, obesity, ischemic heart diseases, ischemic brain disorders, and peripheral arterial embolism.

What is claimed is:

1. A method of sequestering a 14-3-3 protein with a substance which inhibits the interaction with IRS-1 protein or IRS-2 protein comprising contacting the 14-3-3 protein with said substance in an amount sufficient to sequester said 14-3-3 protein, wherein said substance is a peptide selected from the group consisting of SEQ ID NO:2, SEQ ID NO:3, and SEQ ID NO:4.

2. The method of claim 1, wherein said IRS-1 protein comprises the amino acids in SEQ ID NO:1.

3. The method of claim 1, wherein said IRS-2 protein comprises the amino acids in SEQ ID NO:5.

4. The method of claim 1, wherein said peptide is SEQ ID NO:2.

5. The method of claim 1, wherein said peptide is SEQ ID NO:3.

6. The method of claim 1, wherein said peptide is SEQ ID NO:4.

7. The method of claim 1, wherein said contacting comprises administering said substance to a cell.

8. The method of claim 7, wherein said cell is in a patient.

9. The method of claim 8, wherein said patient is suffering from a disease caused by insulin resistance.

10. A method of inhibiting the interaction between a 14-3-3 protein and IRS protein comprising contacting the 14-3-3 protein with said substance in an amount sufficient to inhibit said interaction, wherein said substance is a peptide selected from the group consisting of SEQ ID NO:2, SEQ ID NO:3, and SEQ ID NO:4.

11. The method of claim 10, wherein said IRS-1 protein comprises the amino acids in SEQ ID NO:1.

12. The method of claim 10, wherein said IRS-2 protein comprises the amino acids in SEQ ID NO:5.

13. The method of claim 10, wherein said peptide is SEQ ID NO:2.

14. The method of claim 10, wherein said peptide is SEQ ID NO:3.

15. The method of claim 10, wherein said peptide is SEQ ID NO:4.

16. The method of claim 10, wherein said contacting comprises administering said substance to a cell.

17. The method of claim 16, wherein said cell is in a patient.

18. The method of claim 17, wherein said patient is suffering from a disease caused by insulin resistance.

* * * * *

SEQUENCE LISTING

```
<160> NUMBER OF SEQ ID NOS: 5

<210> SEQ ID NO 1
<211> LENGTH: 1242
<212> TYPE: PRT
<213> ORGANISM: Homo sapiens

<400> SEQUENCE: 1

Met Ala Ser Pro Pro Glu Ser Asp Gly Phe Ser Asp Val Arg Lys Val
1               5                   10                  15

Gly Tyr Leu Arg Lys Pro Lys Ser Met His Lys Arg Phe Phe Val Leu
            20                  25                  30

Arg Ala Ala Ser Glu Ala Gly Gly Pro Ala Arg Leu Glu Tyr Tyr Glu
        35                  40                  45

Asn Glu Lys Lys Trp Arg His Lys Ser Ser Ala Pro Lys Arg Ser Ile
    50                  55                  60

Pro Leu Glu Ser Cys Phe Asn Ile Asn Lys Arg Ala Asp Ser Lys Asn
65                  70                  75                  80

Lys His Leu Val Ala Leu Tyr Thr Arg Asp Glu His Phe Ala Ile Ala
                85                  90                  95

Ala Asp Ser Glu Ala Glu Gln Asp Ser Trp Tyr Gln Ala Leu Leu Gln
            100                 105                 110

Leu His Asn Arg Ala Lys Gly His His Asp Gly Ala Ala Ala Leu Gly
        115                 120                 125

Ala Gly Gly Gly Gly Ser Cys Ser Gly Ser Ser Gly Leu Gly Glu
    130                 135                 140

Ala Gly Glu Asp Leu Ser Tyr Gly Asp Val Pro Pro Gly Pro Ala Phe
145                 150                 155                 160

Lys Glu Val Trp Gln Val Ile Leu Lys Pro Lys Gly Leu Gly Gln Thr
                165                 170                 175

Lys Asn Leu Ile Gly Ile Tyr Arg Leu Cys Leu Thr Ser Lys Thr Ile
            180                 185                 190

Ser Phe Val Lys Leu Asn Ser Glu Ala Ala Ala Val Val Leu Gln Leu
        195                 200                 205

Met Asn Ile Arg Arg Cys Gly His Ser Glu Asn Phe Phe Phe Ile Glu
    210                 215                 220

Val Gly Arg Ser Ala Val Thr Gly Pro Gly Glu Phe Trp Met Gln Val
225                 230                 235                 240

Asp Asp Ser Val Val Ala Gln Asn Met His Glu Thr Ile Leu Glu Ala
                245                 250                 255

Met Arg Ala Met Ser Asp Glu Phe Arg Pro Arg Ser Lys Ser Gln Ser
            260                 265                 270
```

-continued

```
Ser Ser Asn Cys Ser Asn Pro Ile Ser Val Pro Leu Arg Arg His His
            275                 280                 285
Leu Asn Asn Pro Pro Pro Ser Gln Val Gly Leu Thr Arg Arg Ser Arg
    290                 295                 300
Thr Glu Ser Ile Thr Ala Thr Ser Pro Ala Ser Met Val Gly Gly Lys
305                 310                 315                 320
Pro Gly Ser Phe Arg Val Arg Ala Ser Ser Asp Gly Glu Gly Thr Met
                325                 330                 335
Ser Arg Pro Ala Ser Val Asp Gly Ser Pro Val Ser Pro Ser Thr Asn
            340                 345                 350
Arg Thr His Ala His Arg His Arg Gly Ser Ala Arg Leu His Pro Pro
            355                 360                 365
Leu Asn His Ser Arg Ser Ile Pro Met Pro Ala Ser Arg Cys Ser Pro
    370                 375                 380
Ser Ala Thr Ser Pro Val Ser Leu Ser Ser Ser Thr Ser Gly His
385                 390                 395                 400
Gly Ser Thr Ser Asp Cys Leu Phe Pro Arg Arg Ser Ser Ala Ser Val
                405                 410                 415
Ser Gly Ser Pro Ser Asp Gly Gly Phe Ile Ser Ser Asp Glu Tyr Gly
            420                 425                 430
Ser Ser Pro Cys Asp Phe Arg Ser Ser Phe Arg Ser Val Thr Pro Asp
            435                 440                 445
Ser Leu Gly His Thr Pro Pro Ala Arg Gly Glu Glu Glu Leu Ser Asn
    450                 455                 460
Tyr Ile Cys Met Gly Gly Lys Gly Pro Ser Thr Leu Thr Ala Pro Asn
465                 470                 475                 480
Gly His Tyr Ile Leu Ser Arg Gly Gly Asn Gly His Arg Cys Thr Pro
                485                 490                 495
Gly Thr Gly Leu Gly Thr Ser Pro Ala Leu Ala Gly Asp Glu Ala Ala
            500                 505                 510
Ser Ala Ala Asp Leu Asp Asn Arg Phe Arg Lys Arg Thr His Ser Ala
            515                 520                 525
Gly Thr Ser Pro Thr Ile Thr His Gln Lys Thr Pro Ser Gln Ser Ser
    530                 535                 540
Val Ala Ser Ile Glu Glu Tyr Thr Glu Met Met Pro Ala Tyr Pro Pro
545                 550                 555                 560
Gly Gly Gly Ser Gly Gly Arg Leu Pro Gly His Arg His Ser Ala Phe
                565                 570                 575
Val Pro Thr Arg Ser Tyr Pro Glu Glu Gly Leu Glu Met His Pro Leu
            580                 585                 590
Glu Arg Arg Gly Gly His His Arg Pro Asp Ser Ser Thr Leu His Thr
            595                 600                 605
Asp Asp Gly Tyr Met Pro Met Ser Pro Gly Val Ala Pro Val Pro Ser
    610                 615                 620
Gly Arg Lys Gly Ser Gly Asp Tyr Met Pro Met Ser Pro Lys Ser Val
625                 630                 635                 640
Ser Ala Pro Gln Gln Ile Ile Asn Pro Ile Arg Arg His Pro Gln Arg
                645                 650                 655
Val Asp Pro Asn Gly Tyr Met Met Met Ser Pro Ser Gly Gly Cys Ser
            660                 665                 670
Pro Asp Ile Gly Gly Gly Pro Ser Ser Ser Ser Ser Ser Asn Ala
            675                 680                 685
```

-continued

Val Pro Ser Gly Thr Ser Tyr Gly Lys Leu Trp Thr Asn Gly Val Gly
690                 695                 700

Gly His His Ser His Val Leu Pro His Pro Lys Pro Val Glu Ser
705                 710                 715                 720

Ser Gly Gly Lys Leu Leu Pro Cys Thr Gly Asp Tyr Met Asn Met Ser
                725                 730                 735

Pro Val Gly Asp Ser Asn Thr Ser Pro Ser Asp Cys Tyr Tyr Gly
                740                 745                 750

Pro Glu Asp Pro Gln His Lys Pro Val Leu Ser Tyr Tyr Ser Leu Pro
                755                 760                 765

Arg Ser Phe Lys His Thr Gln Arg Pro Gly Glu Pro Glu Glu Gly Ala
770                 775                 780

Arg His Gln His Leu Arg Leu Ser Thr Ser Ser Gly Arg Leu Leu Tyr
785                 790                 795                 800

Ala Ala Thr Ala Asp Asp Ser Ser Ser Thr Ser Ser Asp Ser Leu
                805                 810                 815

Gly Gly Gly Tyr Cys Gly Ala Arg Leu Glu Pro Ser Leu Pro His Pro
                820                 825                 830

His His Gln Val Leu Gln Pro His Leu Pro Arg Lys Val Asp Thr Ala
                835                 840                 845

Ala Gln Thr Asn Ser Arg Leu Ala Arg Pro Thr Arg Leu Ser Leu Gly
850                 855                 860

Asp Pro Lys Ala Ser Thr Leu Pro Arg Ala Arg Glu Gln Gln Gln Gln
865                 870                 875                 880

Gln Gln Pro Leu Leu His Pro Glu Pro Lys Ser Pro Gly Glu Tyr
                885                 890                 895

Val Asn Ile Glu Phe Gly Ser Asp Gln Ser Gly Tyr Leu Ser Gly Pro
                900                 905                 910

Val Ala Phe His Ser Ser Pro Ser Val Arg Cys Pro Ser Gln Leu Gln
                915                 920                 925

Pro Ala Pro Arg Glu Glu Glu Thr Gly Thr Glu Glu Tyr Met Lys Met
930                 935                 940

Asp Leu Gly Pro Gly Arg Arg Ala Ala Trp Gln Glu Ser Thr Gly Val
945                 950                 955                 960

Glu Met Gly Arg Leu Gly Pro Ala Pro Pro Gly Ala Ala Ser Ile Cys
                965                 970                 975

Arg Pro Thr Arg Ala Val Pro Ser Ser Arg Gly Asp Tyr Met Thr Met
                980                 985                 990

Gln Met Ser Cys Pro Arg Gln Ser Tyr Val Asp Thr Ser Pro Ala Ala
                995                 1000                1005

Pro Val Ser Tyr Ala Asp Met Arg Thr Gly Ile Ala Ala Glu Glu
                1010                1015                1020

Val Ser Leu Pro Arg Ala Thr Met Ala Ala Ala Ser Ser Ser Ser
                1025                1030                1035

Ala Ala Ser Ala Ser Pro Thr Gly Pro Gln Gly Ala Ala Glu Leu
                1040                1045                1050

Ala Ala His Ser Ser Leu Leu Gly Gly Pro Gln Gly Pro Gly Gly
                1055                1060                1065

Met Ser Ala Phe Thr Arg Val Asn Leu Ser Pro Asn Arg Asn Gln
                1070                1075                1080

Ser Ala Lys Val Ile Arg Ala Asp Pro Gln Gly Cys Arg Arg Arg
                1085                1090                1095

His Ser Ser Glu Thr Phe Ser Ser Thr Pro Ser Ala Thr Arg Val

```
                    1100                1105                1110

Gly Asn  Thr Val Pro Phe  Gly Ala Gly Ala Val   Gly Gly Gly
    1115              1120              1125

Gly Gly  Ser Ser Ser Ser  Ser Glu Asp Val Lys   Arg His Ser Ser
    1130              1135              1140

Ala Ser  Phe Glu Asn Val  Trp Leu Arg Pro Gly   Glu Leu Gly Gly
    1145              1150              1155

Ala Pro  Lys Glu Pro Ala  Lys Leu Cys Gly Ala   Ala Gly Gly Leu
    1160              1165              1170

Glu Asn  Gly Leu Asn Tyr  Ile Asp Leu Asp Leu   Val Lys Asp Phe
    1175              1180              1185

Lys Gln  Cys Pro Gln Glu  Cys Thr Pro Glu Pro   Gln Pro Pro Pro
    1190              1195              1200

Pro Pro  Pro Pro His Gln  Pro Leu Gly Ser Gly   Glu Ser Ser Ser
    1205              1210              1215

Thr Arg  Arg Ser Ser Glu  Asp Leu Ser Ala Tyr   Ala Ser Ile Ser
    1220              1225              1230

Phe Gln  Lys Gln Pro Glu  Asp Arg Gln
    1235              1240

<210> SEQ ID NO 2
<211> LENGTH: 15
<212> TYPE: PRT
<213> ORGANISM: Artificial Sequence
<220> FEATURE:
<221> NAME/KEY: misc_feature
<223> OTHER INFORMATION: Description of Artificial Sequence:synthetic
      peptide
<221> NAME/KEY: MOD_RES
<222> LOCATION: (9)..(9)
<223> OTHER INFORMATION: PHOSPHORYLATION

<400> SEQUENCE: 2

Asp Glu Phe Arg Pro Arg Ser Lys Ser Gln Ser Ser Ser Asn Cys
1               5                   10                  15

<210> SEQ ID NO 3
<211> LENGTH: 15
<212> TYPE: PRT
<213> ORGANISM: Artificial Sequence
<220> FEATURE:
<221> NAME/KEY: misc_feature
<223> OTHER INFORMATION: Description of Artificial Sequence:synthetic
      peptide
<221> NAME/KEY: MOD_RES
<222> LOCATION: (9)..(9)
<223> OTHER INFORMATION: PHOSPHORYLATION

<400> SEQUENCE: 3

His Pro Pro Leu Asn His Ser Arg Ser Ile Pro Met Pro Ala Ser
1               5                   10                  15

<210> SEQ ID NO 4
<211> LENGTH: 15
<212> TYPE: PRT
<213> ORGANISM: Artificial Sequence
<220> FEATURE:
<221> NAME/KEY: misc_feature
<223> OTHER INFORMATION: Description of Artificial Sequence:synthetic
      peptide
<221> NAME/KEY: MOD_RES
<222> LOCATION: (9)..(9)
<223> OTHER INFORMATION: PHOSPHORYLATION

<400> SEQUENCE: 4
```

-continued

```
Met Pro Met Ser Pro Lys Ser Val Ser Ala Pro Gln Gln Ile Ile
1               5                   10                  15
```

<210> SEQ ID NO 5
<211> LENGTH: 159
<212> TYPE: PRT
<213> ORGANISM: Homo sapiens

<400> SEQUENCE: 5

```
Glu Val Trp Gln Val Asn Leu Lys Pro Lys Gly Leu Gly Gln Ser Lys
1               5                   10                  15

Asn Leu Thr Gly Val Tyr Arg Leu Cys Leu Ser Ala Arg Thr Ile Gly
                20                  25                  30

Phe Val Lys Leu Asn Cys Glu Gln Pro Ser Val Thr Leu Gln Leu Met
                35                  40                  45

Asn Ile Arg Arg Cys Gly His Ser Asp Ser Phe Phe Phe Ile Glu Val
                50                  55                  60

Gly Arg Ser Ala Val Thr Gly Pro Gly Glu Leu Trp Met Gln Ala Asp
65                  70                  75                  80

Asp Ser Val Val Ala Gln Asn Ile His Glu Thr Ile Leu Glu Ala Met
                85                  90                  95

Lys Ala Leu Lys Glu Leu Phe Glu Phe Arg Pro Arg Ser Lys Ser Gln
                100                 105                 110

Ser Ser Gly Ser Ser Ala Thr His Pro Ile Ser Val Pro Gly Ala Arg
                115                 120                 125

Arg His His His Leu Val Asn Leu Pro Pro Ser Gln Thr Gly Leu Val
                130                 135                 140

Arg Arg Ser Arg Thr Asp Ser Leu Ala Ala Thr Pro Pro Ala Ala
145                 150                 155
```